(12) United States Patent
Jensen

(10) Patent No.: US 6,558,909 B2
(45) Date of Patent: May 6, 2003

(54) HAEMOBARTONELLA PCR METHODS AND MATERIALS

(75) Inventor: Wayne A. Jensen, Wellington, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/927,904

(22) Filed: Aug. 10, 2001

(65) Prior Publication Data

US 2002/0081615 A1 Jun. 27, 2002

Related U.S. Application Data

(63) Continuation of application No. 09/398,577, filed on Sep. 17, 1999, now abandoned.
(60) Provisional application No. 60/100,987, filed on Sep. 18, 1998.

(51) Int. Cl.[7] ............................ C12Q 1/68; C12P 19/34; C07H 21/04
(52) U.S. Cl. .................. 435/6; 435/91.2; 536/23.7; 536/24.32; 536/24.33
(58) Field of Search ............................ 435/6, 15, 91.2; 536/23.7, 24.32, 24.33

(56) References Cited

PUBLICATIONS

Minnick & Barbian, 31 *J Microb Meth* 51 (1997).
Bass, et al., 16 *Pediatr. Infect. Dis. J.* 163 (1997).
Kordick, et al., 35(7) *J. Clin. Microb.* 1813 (1997).
Joblet, et al., 33(7) *J. Clin. Microb.* 1879 (1995).
Norman, et al., 33(7) *J. Clin. Microb.* 1797 (1995).
Birtles, 129 *FEMS Microbiol. Letters* 261 (1995).
Matar, et al., 31(7) *J. Clin. Microb.* 1730 (1993).
Roux & Raoult, 33(6) *J. Clin. Microb.* 1573 (1995).
Rikihisa, et al., 35(4) *J. Clin. Microb.* 823 (1997).
Messick, et al., 36(2) *J. Clin. Microb.* 462 (1998).
Dawson, et al., 156 *Arch Intern Med* 137 (1996).
Warner & Dawson, *Genus and Species–Level Identification of Ehrlichia Species by PCR and Sequencing*, Protocol 2 from ASM Press, Washington, DC (1996).
Dawson, et al., *Polymerase Chain Reaction Evidence of Ehrlichia chafeensis, an etiologic agent of human ehrlichiosis, in dogs from southeast Virginia*, 57(8) *Amer. J. Vet. Res.* 1175 (1996).
Dawson, et al., 57(1) *Am J Trop Med Hyg* 109 (1997).

*Primary Examiner*—Carla J. Myers
*Assistant Examiner*—Diana Johannsen
(74) *Attorney, Agent, or Firm*—Heska Corporation

(57) ABSTRACT

In broad terms, the present invention includes materials and methods useful to distinguish between and among species of a genus. The present methods utilize the differences in PCR amplicon sizes to specifically identify a given species.

13 Claims, No Drawings

SEQUENCE LISTING

<160> NUMBER OF SEQ ID NOS: 6

<210> SEQ ID NO 1
<211> LENGTH: 22
<212> TYPE: DNA
<213> ORGANISM: Haemobartonella felis

<400> SEQUENCE: 1
acgaaagtct gatggagcaa ta                 22

<210> SEQ ID NO 2
<211> LENGTH: 22
<212> TYPE: DNA
<213> ORGANISM: Haemobartonella felis

<400> SEQUENCE: 2
acgcccaata aatccgrata at                 22

<210> SEQ ID NO 3
<211> LENGTH: 14
<212> TYPE: DNA
<213> ORGANISM: Artificial sequence
<220> FEATURE:
<223> OTHER INFORMATION: Synthetic Primer

<400> SEQUENCE: 3
ctgatggagc aata                                                      14

<210> SEQ ID NO 4
<211> LENGTH: 14
<212> TYPE: DNA
<213> ORGANISM: Artificial sequence
<220> FEATURE:
<223> OTHER INFORMATION: Synthetic Primer

<400> SEQUENCE: 4
taaatccgra taat                                                      14

<210> SEQ ID NO 5
<211> LENGTH: 1377
<212> TYPE: DNA
<213> ORGANISM: Haemobartonella felis

<400> SEQUENCE: 5
agatttgatc ctggctcaga attaatgctg atggtatgcc taatacatgc aagtcgaacg      60
gatcttggtt tcggccaaga ttagtggcaa acgggtgagt aatacatatc taacatgccc     120
ctctgtgggg gatagccgct tgaaaaagcg attaataccc cataggaagc tttatctatg     180
atttagcttt taaagccttc gggcgctgag ggattgggat atgctctatt agctagttgg     240
cgggataaaa gcccaccaag gcaatgatag atagctggtc ttagaggatg aacagccaca     300
atgggattga gatacggccc atattcctac gggaagcagc agtagggaat cttccacaat     360
ggacgaaagt ctgatggagc ataccatgt gaacgatgaa ggccttttg gttgtaaagt     420
tcttttacga gggataatta tgatagtact tgctgaataa gtgacagcaa actatgtgcc     480
agcagctgcg gtaatacata ggtcgcgagc attattcgga tttattgggc gtaaagcaag     540
cgcaggcgga tgttgtaagt tctgtgttaa atgcagctac tcaatagttg tatgcaccga     600
atactacatg tctagattgt ggtagggagt ttcggaatta agcatggagc ggtggaatgt     660
gtagatatgc ttaagaacac cagaggcgaa ggcggaaact taggccataa atgacgttta     720
ggcttgaaag tgtggggagc aaatgggatt agataccccca gtagtccaca ccgtaaacga     780
tgggtattag atattagggc tttagcttta gtgttgtagc ttacgcgtta aatacccgc      840
ctgggtagta catatgcaaa tatgaaactc aaaggaattg acggggacct gaacaagtgg     900
tggagcatgt tgcttaattc gataatacac gaaaaacctt accaaggttt gacatccctc     960
gcaaagctat agaaatatag tagaggttat cgaggtgaca ggtggtgcat ggctgtcgtc    1020
agctcgtgtc ttgagatgtt tggttaagtc ccgcaacgag cgcaacccca ctctttagtt    1080
acttgtctaa agagactgca cagtaatgta gaggaaggat gggatcacgt caagtcatca    1140
tgcccttat gccttgggct gcaaacgtgc tacaatggcg aacacaatgt gttgcaaacc     1200
agcgatggta agctaatcac caaatttcgt ctcagttcgg ataggaggct gcaattcgcc    1260
tccttgaagt tggaatcact agtaatcccg tgtcagctat atcggggtga atccgttccc    1320
aggtcttgta cacaccgccc gtcaaactat gagaggagtg ggcatttaaa aatacat       1377

```
<210> SEQ ID NO 6
<211> LENGTH: 1430
<212> TYPE: DNA
<213> ORGANISM: Haemobartonella felis

<400> SEQUENCE: 6
ctcaggatta atgctggtgg tatgcataac acatgcaagt cgaacgaaga gggtttactc      60
tcttagtggc gaacgggcga gtaacacata tttaacttac ctgcacgagg agaatagcaa     120
ctcgaaagag ttattaatac tccataggtt tgagacccaa attaaaggga gcgaactggg     180
aaactagagc ttcgcgagca gagaggagta tgtcctatta ggttgttggt ggggtaattg     240
cctaccaagc cgatgatggg tagctggact gagaggtcga ccagccgcaa tgggattgaa     300
atacggccca tattcctacg ggaagcagca gtgaggaatt ttccacaatg gacgaaagtc     360
tgatggagca ataccatgtg aacgatgaag gtcttctgat tgtaaagttc ttttatttag     420
gaaaaaaagc ttgataggaa atgattaagc cttgattgta ctaaatgaat aagtgacagc     480
taactatgtg ccagcagctg cggtaaaaca taggtcacga gcattatccg gatttattgg     540
gcgtaaagga agcgtaggcg gacaaattga tctattgtta aaggcacttg ctcaacgagt     600
tgtttgtgat agatatcgtt tgtctagaat tagttaggag atactggaat tcaatgtgta     660
gcggtggaat gcgtagatat attgaggaac accggaggct aaggcgagta tctaggacat     720
aattgacgct gaggcttgaa agcgtgggga gcaaatggga ttagataccc cagtagtcca     780
cgccgtaaac gatgggtatt aggtatttgg tctaggactg agtgctgtag ctaacgcgtt     840 aaatacccg cctgggtagt atatatgcaa atatgaaact caaagaaatt gacggggacc      900
tgaacaagtg gtggagcatg ttgcttaatt cgataataca cgaaaaacct taccgaggct     960
tgtaatcttt tgcgaagcta tagaaatata gtggaggtta tcagaatgac aggtggtgca    1020
tggctgtcgt cagctcgtgt cttgagatgt ttggttaagt cccgtaacga gcgcaaccct    1080
tctctttagt taaatagttc taaagtgact gaatcgtaag atataggaag gctggggcca    1140
agtcaagtca tcatgcccct tatgcctcgg gctgcaaacg tgctacaatg gtaggcataa    1200
tgtgtcgcaa tctagaaata gggagctaat caccgaaaac ctatctcagt ccggataaaa    1260
ggctgcaatt cgcctatttg aagttggaat cactagtaat cctgtgtcag ctatatcagg    1320
gtgaatgcgt tcccaggtct tgtacacacc gcccgtcaaa ctatgggaga aagtactagt    1380
tgaaaccgta ttaaattacg tctagattgg taattttgac tggagttaag              1430
```

HAEMOBARTONELLA PCR METHODS AND MATERIALS

CROSS-REFERENCE TO RELATED APPLICATIONS

This invention is a continuation of copending application Ser. No. 09/398,577, now abandoned, filed Sep. 17, 1999, which claims priority to U.S. Provisional Application Serial No. 60/100,987, filed Sep. 18, 1998, each entitled "HAEMOBARTONELLA PCR METHODS AND MATERIALS".

BACKGROUND OF THE INVENTION

The present invention is concerned with speciation of organisms, for the purpose of improving differential diagnosis of disease. The assays currently available to distinguish between or among species have not always met the expectations of consumers because they are either too costly, cumbersome or unavailable.

Polymerase chain reaction (PCR) and serological assays are currently used to distinguish among species. Serological tests present problems with cross-reactivity and available PCR tests are complicated. Typically, PCR-based assays require three steps: 1) conducting PCR using a primer set which distinguishes among members of different genera, but not among members of the same genus; 2) digesting the PCR products with restriction enzymes and 3) distinguishing among species on the basis of restriction digest patterns. One assay uses several sets of species-specific primers instead of digestion with restriction enzymes, with identification of the PCR products made by amplicon size. Minnick and Barbian, 31 *J Microb Meth* 51 (1997).

*Haemobartonella felis*, which causes infectious feline anemia, has two known subspecies: the California subspecies and the Ohio/Florida (herein called "Ohio") subspecies. Other organisms also cause anemia (eg. Bartonella and Ehrlichia), but treatment of the anemia is ideally directed to the causative organism. PCR technology has been used to detect *Haemobartonella felis*, although distinguishing between anemia-causing subspecies has not been accomplished.

In Rikihisa et al., 35 (4) *J. Clin. Micros.* 823 (1997), there is disclosed the use of portions of conserved 16S sequences as primers in order to sequence the 16S genes of *H. felis* California and *H. felis* Ohio, and evolutionarily compare them to each other as well as to other organisms. It also discloses a method for distinguishing *H. felis* strains from one another, which method requires restriction enzyme cleavage and gel electrophoresis. In Messick et al., 36 (2) *J. Clin. Microb.* 462 (1998), there are disclosed primers useful to identify (selectively) *H. felis* Ohio. It does not identify an assay for distinguishing *H. felis* Ohio and *H. felis* California or other organisms from *H. felis* Ohio.

In another organism, Bartonella PCR assays have been discussed which use differences in citrate synthase sequences. These assays use a first step of conducting PCR and a second step of digesting the PCR products with restriction enzymes to distinguish among species. Joblet et al., 33(7) *J. Clin. Microb.* 1879 (1995); Norman et al., 33(7) *J. Clin. Microb.* 1797 (1995). PCR assays on the basis of differences in 16S rRNA sequences in Bartonella have also been conducted, using restriction enzymes to distinguish among species. Birtles, 129 *FEMS Microbiol. Letters* 261 (1995).

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

The present invention requires only a single step to generate amplicons which identify a specific species.

It is therefore an object to provide a simplified assay for distinguishing between or among Haemobartonella species.

It is yet another object to provide materials related to the methods disclosed, including primer sets.

In all of the above embodiments, it is an object to provide methods to diagnose disease using the materials and methods provided.

It is also an object to provide methods for identifying primers useful to conduct PCR assays which capitalize on the species-specific size differences in the 16S region of Haemobartonella.

Finally, it is an object of the invention to provide a kit for convenient use of the materials and methods herein provided.

Definitions: For the purposes of the present invention, the following terms shall have the following definitions:

"Amplicon(s)" shall mean a nucleic acid produced through use of primers in PCR.

"Genus-specific primer(s)" shall mean primers being capable of amplifying an amplicon from at least a portion of the 16S region of at least two Haemobartonella species, and no other genera, and wherein the size of the amplicon is unique to the species.

When the term "Genus-specific primer(s)" is used to describe primers used in PCR assays, it is assumed that said primers are also being in amounts sufficient to amplify at least one ascertainable fragment.

A "set" of primers means at least one forward and at least one reverse primer, that when used in a PCR assay in appropriate amounts and in the presence of amplifiable nucleic acid, is capable of amplifying nucleic acid.

"Species" means any species or subspecies, or other subset of species or subspecies.

DETAILED DESCRIPTION OF THE INVENTION

In broad terms, the present invention includes materials and methods useful to distinguish between and among species of a genus. The methods simplify and are therefore more cost-effective than previous methods. In addition, because the present methods are simpler than previous methods, the risk of operator error, contamination, or any other technical problem is reduced, making the present invention inherently more reliable than previous methods.

The present invention also includes methods to detect Haemobartonella species in a test sample, comprising: a.) conducting polymerase chain reaction using starting materials which comprise a test sample and at least one set of genus-specific primers; and b.) detecting Haemobartonella species in the test sample in the event a Haemobartonella-sized amplicon is present. A method as described, wherein step b.) comprises gel electrophoresis is preferred, although any method for detecting amplicon(s) (e.g. size-differentiating chromatography) is within the scope of the present invention.

For instance, the above method can be used to identify both the specific presence, or the specific absence of a certain species of Haemobartonella. As an example, the present method could be used to test a sample using a primer set (one forward sequence, one reverse sequence, in amounts necessary to conduct PCR) designed to amplify, both *H. felis* Ohio and *H. felis* California, although the size of the amplicons would differ. In that instance, it is possible that the primers would amplify an amplicon unique for *H. felis* Ohio, and not *H. felis* California. The result would indicate the presence of *H. felis* Ohio as well as the absence of *H. felis* California. In fact, methods as described, wherein the primers are capable of amplifying uniquely-sized amplicons from *H. felis* Ohio and *H. felis* California is a preferred embodiment of the present invention. However, methods wherein the primers are capable of amplifying uniquely-sized amplicons for every Haemobartonella species are also preferred.

Moreover, the present invention is not limited to the use of only one set of genus-specific primers. The methods herein also include those wherein a second set of primers is used, for example, for nested PCR. However, methods wherein PCR is conducted using one set of genus-specific primers is preferred.

Methods which utilize primers designed using conserved sequences in or flanking the Haemobartonella 16S region are within the scope of the present invention. A preferred region for designing forward primers for the present invention is the region spanning nucleotides 175–425. Not all bases are identical in these regions, but those in the art are aware of primer design strategy in light of non-identical sequences. A preferred region for designing reverse primers for the present invention is the region spanning nucleotides 455–700. Not all bases are identical in these regions, but those in the art are aware of primer design strategy in light of non-identical sequences.

Methods as above wherein the genus-specific forward primer comprises a sequence selected from the group consisting of SEQ ID NO 1 and SEQ ID NO 3 are most preferred. Methods as described in the previous paragraph wherein the Haemobartonella genus-specific reverse primer comprises a sequence selected from the group consisting of SEQ ID NO 2 and SEQ ID NO 4 are most preferred.

Also provided in the present invention are methods to detect Haemobartonella-caused disease in a mammal, comprising: a.) conducting polymerase chain reaction using starting materials which comprise a test sample and at least one set of genus-specific primers; and b.) detecting Haemobartonella-caused disease in the test sample in the event a Haemobartonella-sized amplicon is present. A method as in this paragraph, wherein the Haemobartonella-caused disease is anemia is preferred.

Specifically the present invention also provides methods to detect anemia in a mammal, comprising: a.) conducting polymerase chain reaction using starting materials which comprise at least one set of genus-specific primers capable of amplifying *H. felis* Ohio and *H. felis* California nucleic acid, and a test sample; and b.) detecting feline infectious anemia in the test sample in the event a *H. felis* Ohio or a *H. felis* California-sized amplicon is present.

The genus-specific primers for the above assay can be designed using the *H. felis* Ohio (Genbank Accession Number 95297) sequence, designated herein as SEQ ID NO:5 and the *H. felis* California (Genbank Accession Number 88564) sequence, designated herein as SEQ ID NO:6.

The assays described herein comprise both a PCR step and an amplicon size-determination step. PCR can be conducted according to techniques known to one of skill in the art, including, for example, thermocycle PCR and isothermal PCR. A number of printed publications describe these procedures. For instance Sambrook et al., *Molecular Cloning: A Laboratory Manual* (Cold Spring Harbor Laboratory Press, 1989), Ausubel et al., *Current Protocols in Molecular Biology* (Greene Publishing Associates, Inc., 1993) and Walker et al., 89 *Proc Natl Acad Sci USA* 392 (1992) describe typical parameters. Moreover, journal articles by investigators studying the organisms of interest will typically contain details about PCR amplification of the organisms' nucleic acid.

For example, thermocycle PCR is conducted as follows: a sample is taken for amplification. Then, a thermocycler is used (at alternatingly high and low temperatures) to promote a cycle between a.) dissociation of double stranded nucleic acid; and b.) hybridization of the primers to any sample nucleic acid; and c.) subsequent synthesis of complementary nucleic acid. When the primers are bound to a nucleic acid in the test sample, the polymerase synthesizes a nucleic acid complementary to the sample nucleic acid, and when the primers are not bound, no synthesis takes place. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, milk and feces.

The second step in the described methods of the present invention is a size-determination of the PCR products generated. Size determination can be carried out according to any acceptable method, with gel electrophoresis being preferred. Methods for determining size of PCR products are described in Sambrook, supra and Ausubel, supra. Use of a control (identity known) sample or a sizing ladder is particularly helpful as well.

The primers of the present invention can be designed by aligning 16S regions from at least two Haemobartonella species and identifying primers which would amplify an amplicon having differences in absolute size as well as capable of priming polymerase chain reaction. Moreover, it is known in the art that primers are preferably G-C rich, ideally more than 50% of the bases G or C. The length of the primer is usually chosen to minimize the chances of amplifying non-target nucleic acid, as well as minimize self-hybridization. Primers are typically 17 to 30 bases in length, although there are no absolute rules with regard to length or G-C content. For the purposes of the present invention, other parameters may take precedent over the length or constitution of the primers. Certain computer programs (such as MacVector) are helpful in primer design and PCR condition optimization.

The present invention includes kits useful for distinguishing between or among Haemobartonella species, comprising at least one set of genus-specific primers. The present kits preferably further comprise a gel material, such as, but not limited to, agarose or acrylamide.

Nucleic acid compounds are also provided by the present invention. Specifically, compositions of matter comprising a set of genus-specific primers as described herein are included in the present invention. A particular forward Haemobartonella genus-specific primers comprising a sequence selected from the group consisting of SEQ ID NO 1 and SEQ ID NO 3 are preferred. Particular reverse Haemobartonella genus-specific primers comprising a sequence selected from the group consisting of SEQ ID NO 2 and SEQ ID NO 4 are also preferred.

The sequences described in the sequence listing can be shortened from the 5' end, provided that the resulting sequence does not result in loss of specificity when the shortened sequence is used as a primer. Those shortened primers are also useful as a part of a genus-specific primer set. For example, those primers wherein the 5' terminus of SEQ ID NO 1 or SEQ ID NO 2 is shortened by 1–10 bases are also within the scope of the present invention. Primers wherein the 5' terminus of SEQ ID NO 1 or SEQ ID NO 2 is shortened by 1–8 bases are preferred. SEQ ID NO 3 and SEQ ID NO 4 are most preferred. Any of these sequences can be used as primers in the methods described.

EXAMPLES

Example 1 Identification of Suitable Primers

The 16S gene sequences for H. felis Ohio, H. felis California, B. henselae, B. clarridgeae, M. felis, H. muris, E. coli, S. enteritis, K. pneumoniae and M. muris were aligned to identify regions of homology. The goals of primer selection were to identify primers which would 1) be specific for H. felis (i.e. would not amplify product from other cat pathogens), 2) amplify product from both known isolates of H. felis (subspecies Ohio and California), and 3) be able to differentiate between the two known isolates of H. felis.

The region in the 16S gene identified as a candidate amplicon contained an approximately 25 base pair deletion in the H. felis, subspecies H. felis Ohio, sequence as compared to the subspecies California sequence. This deletion is the basis for differentiating between H. felis subspecies Ohio and California. A forward primer, 5'-(ACGAAAGTCTGATGGAGCAATA-3' (nucleotide numbers 363–384 H. felis, subspecies Ohio, Genbank #95297) (SEQ ID NO 1), and a reverse primer, 5'-ACGCCCAATAAATCCG(A/G)ATAAT-3' (nucleotide numbers 532–511 H. felis, subspecies Ohio, Genbank #95297) (SEQ ID NO 2), were selected to specifically amplify H. felis DNA. The specificity is derived from the 3' end of each primer which is complementary to the 16S gene sequence for H. felis (both subspecies) and incompatible for annealing to the "other pathogen" 16S gene sequences. These primers were designed to amplify 170 and 193 bp products from H. felis subspecies Ohio and California, respectively. This difference in PCR product size allowed easy differentiation of the H. felis subspecies by agar gel electrophoresis.

Example 2 Conducting PCR

DNA was extracted from 200 µl of blood collected from H. felis-infected cats, or from relevant microorganisms obtained from the American Type Culture Collection (Rockville, Md.), using the Qiagen QiaAmp Blood Kit (Qiagen, Valencia, Calif.). PCR reactions were run in 50 µl volumes in the Perkin Elmer GeneAmp 9700 Thermocycler (PE Applied Biosystems (PEAB), Foster City, Calif.). The PCR reaction (50 µl) contained 10 mM Tris-HCl, pH 8.3, 50 mM KCl, 3.5 mM $MgCl_2$, 400 µM dUTP, 200 µM dATP, 200 µM dCTP, and 200 µM dGTP, 2.5 units Taq polymerase (PE Amplitaq Gold, PEAB), 1 unit of Uracil DNA Glycosylase (PEAB), 1.0 µM "forward" (SEQ ID NO 1) and "reverse" (SEQ ID NO 2) primers and 5 µl of Rediload (a commercial loading buffer, Research Genetics, Huntsville Ala.) and 5 µl of template DNA. PCR reactions were optimized using dUTP for prevention of PCR product carryover contamination. Prior to amplification, samples were digested with Uracil DNA Glycosylate for 10 minutes at 20° C., followed by 2 minutes at 95° C. The thermocycling profile was repeated for 45 cycles as follows: denaturation for 1 minute at 95° C., annealing for 1 minute at 60° C., and extension for 30 seconds+1 second/cycle at 72° C.

Example 3 Identifying Organisms Present

PCR products were separated based on size by electrophoresis through 2.5% agarose containing 0.65 µg/ml ethidium bromide. Base-pair markers were used for size reference. Results were documented using the Bio-Rad Insta-Doc Gel Documentation System.

The primers amplified 170 and 193 bp products from H. felis Ohio and H. felis California, respectively. This difference in PCR product size allowed easy differentiation of the H. felis subspecies by agar gel electrophoresis.

Example 4 Prevalance of H. felis

Polymerase chain reaction. Primers that detect a segment of the 165 rRNA gene common to both sequenced strains (California and Ohio) of H. felis were utilized in either a nested PCR or timed-release PCR.

Study group. To solicit participation in this study, veterinarians in different regions of the country were contacted by phone and letter. Blood samples were collected from client-owned cats, placed into EDTA, and transported to the laboratory by overnight courier frozen on dry ice or on a cold pack for PCR testing. Samples from cats with suspected haemobartonellosis (suspect cats) were submitted based on presence of fever, anemia, or cytologic evidence of infection. Samples from cats without clinical suspicion of haemobartonellosis (control cats) were submitted as a cohort to a case with suspected haemobartonellosis or were selected from samples for which a complete blood cell count was performed at the laboratory for other reasons.

Complete blood cell count and cytologic assessment. Complete blood cell count (CBC) data was available for some cats. For samples from cats in Colorado, the CBC was performed at the laboratory and thin blood smears were examined for the presence of H. felis by one of the authors (WR). CBC information from other cats in the study was solicited from the referring veterinarian. Samples for which an entire CBC was present were assumed to have had cytologic examination for hemoparasites. For some samples, thin blood smears were submitted for cytologic examination of red blood cells, but not complete blood cell count. Due to variation in laboratories and reporting methods, only the packed cell volume (PCV) or hematocrit (HCT) and cytologic presence or absence of H. felis were assessed in this study. Samples with a PCV or HCT>25 were considered normal; samples with PCV or HCT<25 were considered anemic.

Statistical evaluation. Based on PCR results, cats were defined as Hflg infected, Hfsm infected, Hflg and Hfsm infected, or H. felis naive (both variants). Frequency distributions for each PCR based category was calculated for cats with and without anemia as well as for cats with suspected H. felis infection and control cats. Results were compared by chi square analysis with statistical significance defined as $P<0.05$.

Results. A total of 220 blood samples were assessed in the study; 82 cats were suspected to have haemobartonellosis and 138 cats were included as controls. Of the samples, the majority came from cats that resided in Colorado. Based on PCR results, 10 cats (4.5%) were infected with Hflg, 28 cats (12.7%) were infected with Hfsm, and 5 cats (2.3%) were infected with Hflg and Hfsm for a overall *H. felis* prevalence of 19.5%. Overall, cats with suspected haemobartonellosis (28.0%) were more likely (P=0.0142) than control cats (14.5%) to be *H. felis* infected (Table 1). Significantly greater numbers of cats suspected to have haemobartonellosis were Hflg infected (P<0.0005) or Hflg and Hfsm infected (P=0.0456) than control cats (Table 1). There was no difference in the prevalence of Hfsm infection between the suspect and control groups. CBC were available for 156 cats; 28 cats were anemic and 128 cats were normal. Of the CBC, the majority were performed at the reference laboratory. Based on overall PCR results, a similar number (P=0.1339) of anemic cats (28.6%) and healthy cats (16.4%) were infected with *H. felis* (Table 2). However, significantly more anemic cats were Hflg infected (P=0.0057) or Hflg and Hfsm infected (P=0.0264) than normal cats (Table 2).

Comparisons of PCR results and red blood cell cytologic examination results are listed in Table 3. Only cats with suspected haemobartonellosis were positive on cytologic examination. Each of these 7 cats was concurrently PCR positive. Conversely, there were 26 samples that were PCR positive but negative on cytologic examination.

TABLE 1

Prevalence of Haemobartonella felis infections in cats

| PCR result | Suspect (n = 82) # positive (%) | Control (n = 138) # positive (%) | Chi square | P value |
|---|---|---|---|---|
| OH+ | 10 (12.2) | 0 (0) | 17.631 | <0.0001* |
| CA+ | 9 (11.0) | 19 (13.8) | 0.361 | 0.5479 |
| OH/CA+ | 4 (4.9) | 1 (0.7) | 3.995 | 0.0456* |
| Total | 23 (28.0) | 20 (14.5) | 6.011 | 0.0142* |

*Statistically significant

TABLE 2

Distribution Haemobartonella felis PCR results in cats with and without anemia

| PCR result | Anemia (n = 28) # positive (%) | Normal (n = 128) # positive (%) | Chi square | P value |
|---|---|---|---|---|
| OH+ | 4 (14.3) | 3 (2.3) | 7.645 | 0.0057* |
| CA+ | 2 (7.1) | 17 (13.3) | 0.809 | 0.3683 |
| OH/CA+ | 2 (7.1) | 1 (0.8) | 4.93 | 0.0264* |
| Any OH+ | 6 (21.4) | 4 (3.1) | 12.83 | 0.0003* |
| Any CA+ | 4 (14.3) | 18 (14.1) | 0.001 | 0.9755 |
| Total | 8 (28.6) | 21 (16.4) | 2.247 | 0.1339 |

*Statistically significant

TABLE 3

Comparison of PCR and cytologic examination of blood smears for diagnosis of haemobartonellosis.

| Result | Suspect (n = 53) # positive (%) | Control (n = 112) # positive (%) | Total (n = 165) # positive (%) |
|---|---|---|---|
| Smear+, OH+ | 5 (9.4) | 0 (0) | 5 (3.0) |
| Smear+, CA+ | 1 (1.9) | 0 (0) | 1 (0.6) |
| Smear+, OH/CA+ | 1 (1.9) | 0 (0) | 1 (0.6) |
| Smear+, Any PCR+ | 7 (13.2) | 0 (0) | 7 (4.2) |
| Smear−, OH+ | 4 (7.5) | 0 (0) | 4 (2.4) |
| Smear−, CA+ | 3 (5.7) | 16 (14.3) | 19 (11.5) |
| Smear−, OH/CA+ | 2 (3.8) | 1 (0.9) | 3 (1.8) |
| Smear−, Any PCR+ | 9 (17.0) | 17 (15.2) | 26 (15.8) |
| Smear−, All PCR− | 37 (69.8) | 95 (84.8) | 132 (80.0) |

Although the present invention has been fully described herein, it is to be noted that various changes and modifications are apparent to those skilled in the art. Such changes and modifications are to be understood as included within the scope of the present invention.

What is claimed is:

1. A method to detect and distinguish between *Haemobartonella felis* Ohio and *Haemobartonella felis* California comprising:

a) conducting polymerase chain reaction amplification so as to generate an amplification product, using starting materials which comprise a test sample and a single pair of primers, wherein said pair of primers specifically amplifies a region of the *H. felis* 16S gene that is approximately 25 base pairs shorter in *H. felis* Ohio as compared to *H. felis* California, such that an *H. felis* Ohio amplification product produced by said polymerase chain reaction amplification is shorter than an *H. felis* California amplification product produced by said polymerase chain reaction amplification, wherein the region of the *H. felis* 16S gene that is approximately 25 base pairs shorter in *H. felis* Ohio is located between nucleotides 384 and 511 of the *H. felis* Ohio 16S gene, and wherein said polymerase chain reaction amplification does not produce an amplification product in the presence of any organism other than *Haemobartonella felis*; and b) detecting the presence of and determining the length of amplification products produced by said polymerase chain reaction amplification of step a), wherein the presence and length of amplification products is indicative of the presence of *H. felis* Ohio and/or *H. felis* California in said test sample, and where the absence of amplification products is indicative of the absence of both *H. felis* Ohio and *H. felis* California in said test sample.

2. The method of claim 1, wherein step b) comprises gel electrophoresis.

3. The method of claim 1, wherein the pair of primers includes a forward primer comprising a sequence selected from the group consisting of SEQ ID NO 1 and SEQ ID NO 3.

4. The method of claim 1, wherein the pair of primers includes a reverse primer comprising a sequence selected from the group consisting of SEQ ID NO 2 and SEQ ID NO 4.

5. A method to detect a *Haemobartonella felis* subspecies comprising:

a) conducting polymerase chain reaction amplification so as to generate an amplification product using starting materials which comprise a test sample and a single pair of primers, wherein said pair of primers specifically amplifies a region of the *H. felis* 16S gene that is approximately 25 base pairs shorter in *H. felis* Ohio as compared to *H. felis* California, such that an *H. felis* Ohio amplification product produced by said polymerase chain reaction amplification is shorter than an *H. felis* California amplification product produced by said polymerase chain reaction amplification, wherein the region of the *H. felis* 16S gene that is approximately 25 base pairs shorter in *H. felis* Ohio is located between nucleotides 384 and 511 of the *H. felis* Ohio 16S gene, and wherein said polymerase chain reaction amplification does not produce an amplification product in the presence of any organism other than *Haemobartonella felis*; and b) detecting *Haemobartonella felis* subspecies in the test sample in the event an amplification product is produced from a nucleic acid molecule present in the test sample, wherein the presence of amplification products is indicative of the presence of *Haemobartonella felis* subspecies, and wherein the absence of amplification products is indicative of the absence of *Haemobartonella felis* subspecies in said test sample.

6. The method of claim 5, wherein the pair of primers includes a forward primer comprising a sequence selected from the group consisting of SEQ ID NO 1 and SEQ ID NO 3.

7. The method of claim 5, wherein the pair of primers includes a reverse primer comprising a sequence selected from the group consisting of SEQ ID NO 2 and SEQ ID NO 4.

8. The method of claim 5, wherein step b) comprises gel electrophoresis.

9. A method to detect *Haemobartonella felis*-caused disease in a mammal, comprising:

a) conducting polymerase chain reaction amplification so as to generate an amplification product using starting materials which comprise a body fluid of a mammal putatively having *Haemobartonella felis*-caused disease and a pair of primers, wherein said pair of primers specifically amplifies a region of the *H. felis* 16S gene that is approximately 25 base pairs shorter in *H. felis* Ohio as compared to *H. felis* California, such that an *H. felis* Ohio amplification product produced by said polymerase chain reaction amplification is shorter than an *H. felis* California amplification product produced by said polymerase chain reaction amplification, wherein the region of the *H. felis* 16S gene that is approximately 25 base pairs shorter in *H. felis* Ohio is located between nucleotides 384 and 511 of the *H. felis* Ohio 16S gene, and wherein said polymerase chain reaction amplification does not produce an amplification product in the presence of any organism other than *Haemobartonella felis*; and b) detecting *Haemobartonella felis*-caused disease in said mammal, wherein the presence of an amplification product of a size indicative of the presence of *Haemobartonella felis* Ohio is indicative of *H. felis*-caused disease, wherein the absence of an amplification product indicates that no *Haemobartonella felis* subspecies is present in the body fluid, and wherein the presence of an amplification product of a size indicative of the presence of *Haemobartonella felis* California is not indicative of *Haemobartonella felis*-caused disease.

10. A method of claim 9, wherein the *Haemobartonella felis*-caused disease is anemia.

11. The method of claim 9, wherein the pair of primers includes a forward primer comprising a sequence selected from the group consisting of SEQ ID NO 1 and SEQ ID NO 3.

12. The method of claim 9, wherein the pair of primers includes a reverse primer comprising a sequence selected from the group consisting of SEQ ID NO 2 and SEQ ID NO 4.

13. The method of claim 9, wherein step b) comprises gel electrophoresis.

\* \* \* \* \*